United States Patent
Gorsuch et al.

(10) Patent No.: US 6,899,692 B2
(45) Date of Patent: May 31, 2005

(54) PLASMAPHERESIS FILTER DEVICE AND CATHETER ASSEMBLY

(75) Inventors: Reynolds G. Gorsuch, Yountville, CA (US); Harold W. Peters, Martinez, CA (US); Harold H. Handley, Jr., Novato, CA (US)

(73) Assignee: Transvivo, Inc., Napa, CA (US)

( * ) Notice: Subject to any disclaimer, the term of this patent is extended or adjusted under 35 U.S.C. 154(b) by 214 days.

(21) Appl. No.: 09/981,783

(22) Filed: Oct. 17, 2001

(65) Prior Publication Data

US 2003/0073946 A1 Apr. 17, 2003

(51) Int. Cl.[7] .............................................. A61M 1/34
(52) U.S. Cl. ..................... 604/6.09; 604/6.04; 604/5.04
(58) Field of Search ................. 604/7, 6.01, 5.04, 604/6.09, 6.16, 6.04; 210/321.79, 321.71, 321.8, 500.23

(56) References Cited

U.S. PATENT DOCUMENTS

| | | | | |
|---|---|---|---|---|
| 4,440,641 A | * | 4/1984 | Ostertag | 210/321.79 |
| 4,769,146 A | * | 9/1988 | Schmidt | 210/321.8 |
| 4,832,034 A | | 5/1989 | Pizziconi et al. | 128/632 |
| 4,950,224 A | | 8/1990 | Gorsuch et al. | 604/4 |
| 5,145,583 A | | 9/1992 | Angleraud et al. | 210/646 |
| 5,151,082 A | | 9/1992 | Gorsuch et al. | 604/4 |
| 5,152,743 A | | 10/1992 | Gorsuch et al. | 604/4 |
| 5,224,926 A | | 7/1993 | Gorsuch et al. | 604/4 |
| 5,284,583 A | * | 2/1994 | Rogut | 210/321.8 |
| 5,605,627 A | | 2/1997 | Carlsen et al. | 210/321.7 |
| 5,716,689 A | * | 2/1998 | Rogut | 428/92 |
| 5,735,809 A | | 4/1998 | Gorsuch | 604/4 |
| 5,968,004 A | | 10/1999 | Gorsuch | 604/4 |
| 5,980,478 A | | 11/1999 | Gorsuch | 604/4 |
| 5,980,481 A | | 11/1999 | Gorsuch | 604/28 |
| 6,013,182 A | * | 1/2000 | Emi et al. | 210/500.23 |
| 6,102,884 A | * | 8/2000 | Squitieri | 604/8 |
| 6,224,765 B1 | * | 5/2001 | Watanabe et al. | 210/321.61 |

FOREIGN PATENT DOCUMENTS

| | | | | |
|---|---|---|---|---|
| EP | 0321448 | * | 6/1989 | B01D/13/04 |
| EP | 0341979 | * | 11/1989 | D01D/5/24 |
| EP | 0 882 494 A1 | | 12/1998 | |
| FR | 2566003 | | 12/1985 | |
| JP | 60-232204 | * | 11/1985 | B01D/13/00 |
| JP | 9323031 | | 12/1997 | |

* cited by examiner

*Primary Examiner*—Jeffrey R. Jastrzab
(74) *Attorney, Agent, or Firm*—Knobbe, Martens, Olson & Bear, LLP

(57) ABSTRACT

A filter device for being implanted in a blood vessel for carrying out in-vivo plasma separation comprises one or more elongated hollow tubes and a plurality of elongated hollow microporous fibers, each fiber having a first and second end secured to one or more of the elongated hollow tubes with the interior lumen of each of the fibers communicating with the interior of the one or more of the hollow tubes, and wherein the fiber wall has a higher mass density zone adjacent to the outer wall surface and a lower mass density zone adjacent to the inner wall surface.

48 Claims, 3 Drawing Sheets

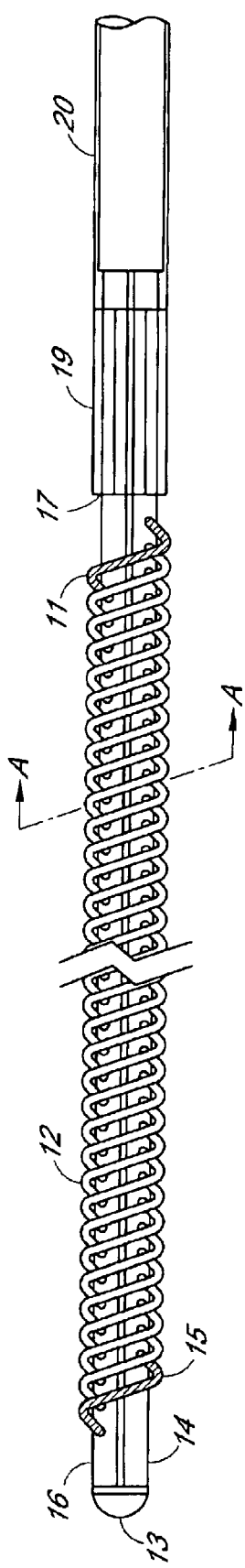
FIG. 1
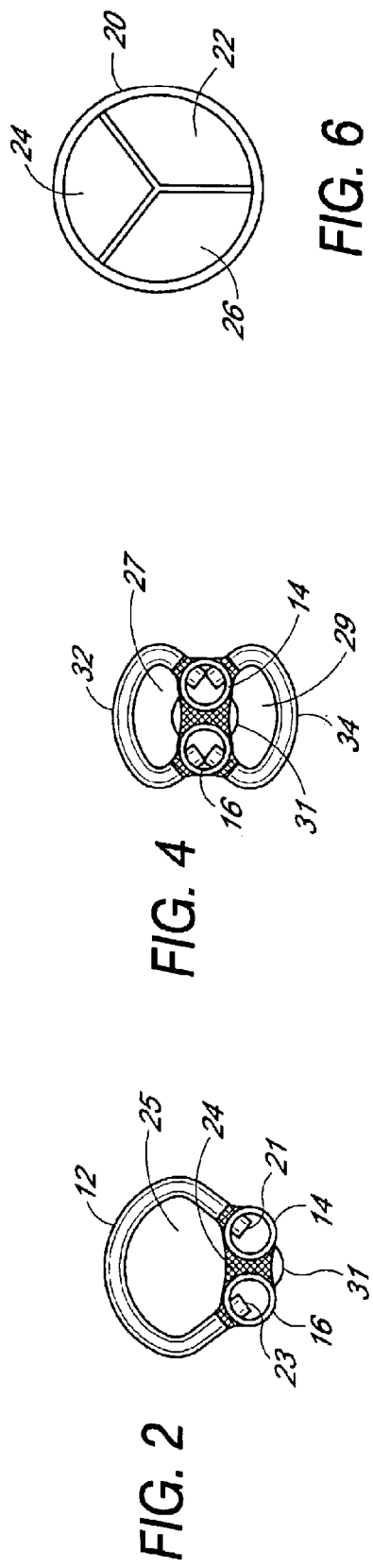
FIG. 6
FIG. 4
FIG. 2
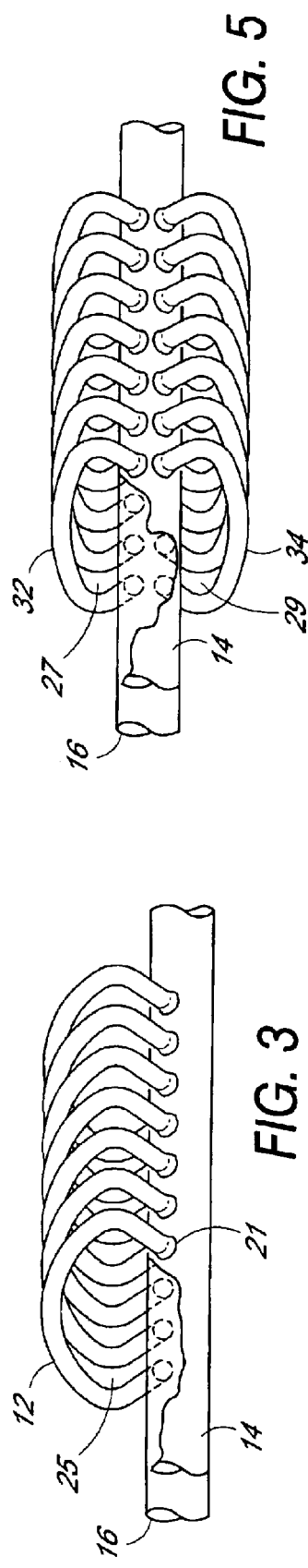
FIG. 5
FIG. 3

PLASMAPHERESIS FILTER DEVICE AND CATHETER ASSEMBLY

BACKGROUND OF THE INVENTION

In U.S. patent application Ser. No. 09/549,131 filed Apr. 13, 2000, (TRANSVI.007A) entitled "Specialized Hollow Fiber Membranes for In-Vivo Plasmapheresis and Ultrafiltration," there are disclosed elongated hollow microporous fibers having an asymmetrical fiber wall characterized by having a lower mass density adjacent to the inner wall surface extending along the interior lumen of the fiber and a higher mass density adjacent to the outer wall surface. Such a fiber wall morphology and pore structure provide unique characteristics necessary for separating blood plasma and/or plasma water in-vivo where continuous extraction of cell-free plasma or ultrafiltered plasma water and its associated toxins is carried out within the blood vessel of a patient or animal. Conventional hollow fibers or filter membranes such as those used in dialysate filter devices are unable to successfully perform in-vivo, intra-vascular plasma separation, becoming clogged within a very short period of time, e.g., minutes, as proteinaceous materials, blood platelets, and other components rapidly occlude the membrane pores. Moreover, conventional dialysate hollow fiber membrane filters do not perform satisfactorily in-vivo because of the relatively high flow rate of blood at the exterior fiber surface and relatively low lumen pressure as compared to dialysate filter apparatus conditions in which plasma separation is carried out at relatively low flow rates and high trans-membrane pressures. For example, typical in-vivo blood flow within a vena cava is about 2.5 L per minute, while blood flow through typical dialysate filter apparatus is nearly stagnant, e.g., about 0.42 ml per minute per fiber. Intravascular trans-membrane pressure is typically about 50 mm Hg or less, as compared to 100–300 mm Hg used in extracorporeal dialysate filters. Conventional dialysate filter membranes have little structural strength which, although acceptable in an encapsulated dialysate filter environment external to the body, are not suitable for introvascular use.

SUMMARY OF THE INVENTION

The present invention relates to a filter device for being implanted in a blood vessel for carrying out in-vivo plasma separation incorporating a plurality of elongated hollow fibers having an asymmetrical fiber wall morphology in which the inner wall surface along the interior fiber lumen has a lower mass density and the fiber wall adjacent to the outer wall surface has a higher mass density. The device comprises one or more elongated hollow conduits or tubes to which opposite ends of each of the fibers are secured so that the interior of the one or more hollow tubes communicates with the interior of each of the elongated hollow fibers. In a preferred embodiment, the device comprises a pair of elongated hollow tubes joined along their length with a first end of each of the hollow fibers secured to and communicating with the interior of one of the hollow tubes, and the second end of each of the fibers secured to and communicating with the interior of the other hollow tube. A plasma or plasma water extraction catheter includes a multiple lumen catheter, preferably a triple lumen catheter, secured to a proximal end of the one or more hollow tubes and communicating with the tube interior for directing blood plasma or plasma water passing through the fiber wall and into the fiber lumen to extracorporeal treatment or collection apparatus or equipment.

BRIEF DESCRIPTION OF THE DRAWINGS

FIG. 1 is a top view of a preferred embodiment of the filter device having a pair of elongated substantially parallel hollow tubes joined together along their length, showing distal and proximal end segments;

FIG. 2 is an enlarged sectional view of the filter device of FIG. 1 along the lines A—A showing a single elongated hollow fiber secured to the hollow tubes;

FIG. 3 is an enlarged side view of a portion of a filter device of the type illustrated in FIG. 1 showing seven elongated hollow fibers secured along the hollow tubes;

FIGS. 4 and 5 are sectional and side views of another filter device embodiment;

FIG. 6 is a sectional view of a triple lumen catheter illustrating the catheter interior;

DETAILED DESCRIPTION OF THE PREFERRED EMBODIMENTS

Figure 7:
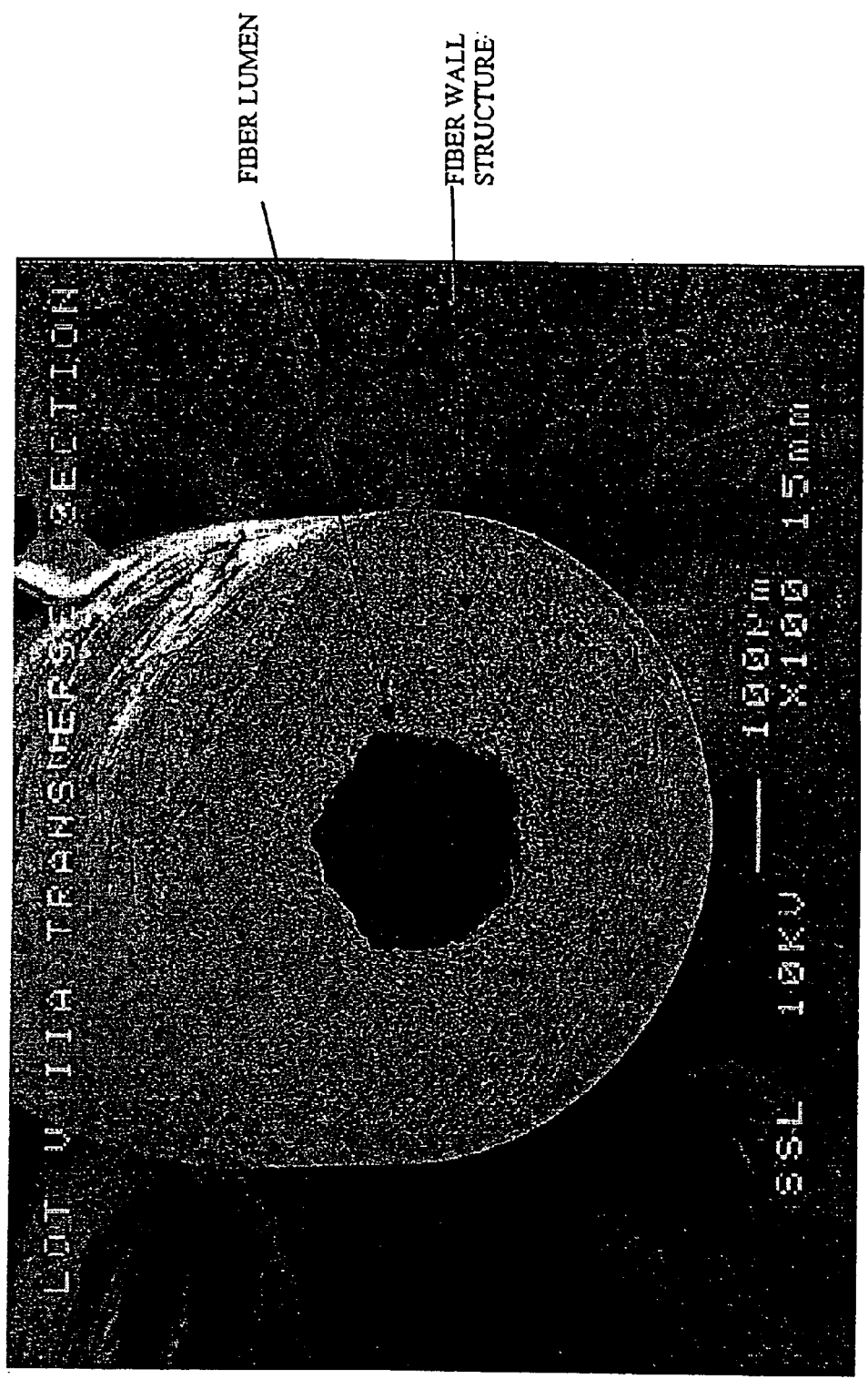
FIG. 7 is a scanning electron microscopy (SEM) image of a cross-section of a typical elongated hollow fiber used in the filter device at 100 µm magnification showing the asymmetrical wall structure between the inner and outer fiber wall surface.

In the preferred embodiment illustrated in FIGS. 1–3, a pair of elongated hollow tubes are joined side-by-side lengthwise to form the core of the filter device. The two elongated hollow core tubes 14 and 16 terminate at a distal end with a distal end plug or cap 13 formed of a material that seals the open tube ends. The tubes and end cap may be made of any suitable biocompatible material, for example, medical grade extruded urethane tubes. Other biocompatible materials include synthetic rubbers, polycarbonate, polyethylene, polypropylene, nylon, etc. The elongated hollow tubes may be secured together using suitable bonding material 24, adhesive compositions, etc., for example, a UV curable adhesive applied along the length between the two tubes. The length and diameter of the filter device may be selected to accommodate the vessel or vein in which it is to be implanted. Accordingly, the diameter and length of the one or more elongated hollow tubes forming the central core of the filter device are selected. A suitable tube length is between about 15 cm and about 25 cm, and preferably between about 18 cm and about 22 cm. Where a pair of core tubes is used as shown in the preferred embodiment, an outer diameter of each tube of between about 1 mm and about 3 mm is suitable. A detectable marker component 31, e.g., a radio opaque material may also be bonded to the device, for example, in bonding material 18 extending along the length of the tubes to assist in implanting and/or monitoring the device especially during insertion and removal.

The elongated hollow microporous fibers used in the filter device are the asymmetrical wall fibers disclosed in U.S. Pat. No. 6,802,820, the descriptions of which are incorporated herein by reference. The morphology of the fiber walls is asymmetrical between the inner fiber lumen and the outer fiber wall which is in direct contact with the blood flowing in the vasculature in which the device is implanted. The filtration performance of such a device is a function of the filter surface of the exposed fibers whereby consideration is given to use larger diameter fibers and to maximize the number of fibers. Thus, it is desirable to use as many individual fibers along the hollow core tubes of the filter device as is practical while maintaining separation of the individual fibers to provide for fluid flow therebetween, and to maximize the amount of outer fiber surface exposed to blood flowing along the length of the filter device. Moreover, the fibers are secured along the length of the hollow tubes in such a manner as to form a fluid flow space between the fibers and the tubes. Again, however, the length of the filter device as well as the overall cross-sectional dimension are tailored or dictated by the blood vessel in which the device is to be used so as to avoid substantial interference with blood flow through the vessel while at the same time be efficient to achieve the intended flow rate of separated plasma.

In a preferred embodiment, the ends of each of the fibers are offset longitudinally relative to one another as illustrated in FIGS. 1–3. As shown, elongated hollow fiber 12 has a first end 21 secured in first elongated hollow tube 14 and second end 23 secured in second hollow tube 16. In the specific device illustrated, the longitudinal spacing between the first and second ends of each fiber is a three-hole or three-fiber offset, e.g., about 0.5 cm. However, with intervals between the adjacent fiber ends of between about 0.1 cm and about 1.0 cm, offsets between first and second fiber ends may be between about 0.3 cm and about 3.0 cm, by way of example. With such offsets between first and second fiber ends, a straight line extending between the ends of a fiber forms an acute angle with an elongated axis of either or both of the elongated hollow tubes, and whereby the fibers also extend lengthwise between their ends along an angle other than 90° relative to the axes of the elongated hollow tubes. The acute angle preferably is between about 45° and about 85°. However, other fiber angles including 90° are not precluded and may be used where desired. In another preferred embodiment shown in FIG. 1, the proximal and distal fibers 11 and 15 located at each end of the filter device are filled with polyurethane or other biocompatible synthetic resin composition. These solid fibers at the ends of the row of fibers protect the adjacent hollow fibers from potential damage caused by mechanical stress during catheter insertion and removal.

In an example of assembly of a filter device, the elongated hollow core tubes 14 and 16 are joined as previously described and holes are drilled at the desired spacing along each of the two tubes. The holes may be drilled along opposite sides of the two tubes, and preferably are spaced at regular intervals of between about 0.1 cm and about 1.0 cm, and more preferably between 0.1 cm and about 0.3 cm. In a device as illustrated in FIGS. 1–3, 6 fibers/cm are used and the interval or spacing between fiber ends along each of the tubes is approximately 1.66 mm. However, other practicable fiber spacing may be used, for example, between about 4 and about 8 fibers/cm and preferably between 5 and 7 fibers/cm of the length of the hollow tubes. The fibers may be secured in the spaced holes by any suitable method. For example, a first fiber end is inserted in a first hole in one of the tubes, the tubes are rotated 180°, and a second end of the fiber inserted in a first hole in the other tube. The procedure is repeated until all fiber ends are inserted in the holes along the two joined tubes. A wire or other elongated member may be inserted along the interior of each of the core tubes during assembly to provide a uniform limit or stop for the fiber ends along the respective hollow tube interior passageways. The fibers are bonded to the tubes and the joints between the fibers and the tubes sealed using a suitable adhesive or potting compound and the wires are removed. In the specific example of a filter device shown in FIG. 1, 118 active hollow fibers and 2 filled end fibers are spaced at 6 fibers/cm along 20.4 cm of the tubes. Each fiber is about 1.5 mm long.

FIGS. 4 and 5 illustrate an alternative embodiment in which fibers are positioned on two sides of the filter device. Fibers 32 and 34 extend at opposite sides of the device whereby first and second ends of each of the fibers are secured along two rows along each of the tubes. As shown in FIGS. 2–5, the fibers are arched to form a space between the fibers and the elongated tubes. In FIGS. 2 and 3, a space 25 is formed by the arched fibers, and in FIGS. 4 and 5, two spaces 27 and 29 are formed by the arched fibers on both sides of the filter device. The length of the fibers may be selected to accommodate the desired filter surface, as well as the desired cross-sectional dimension of the filter device as previously discussed. Suitable fiber lengths are between about 1 mm and about 4 mm to provide sufficient space between the arched fibers and the hollow tubes without distorting the fibers which could cause undesirable strains along the fiber walls or otherwise compromise fiber performance. The location of first and second fiber ends of the embodiment illustrated in FIGS. 4 and 5 may be as described for the embodiment of FIGS. 2 and 3.

Figure 8:
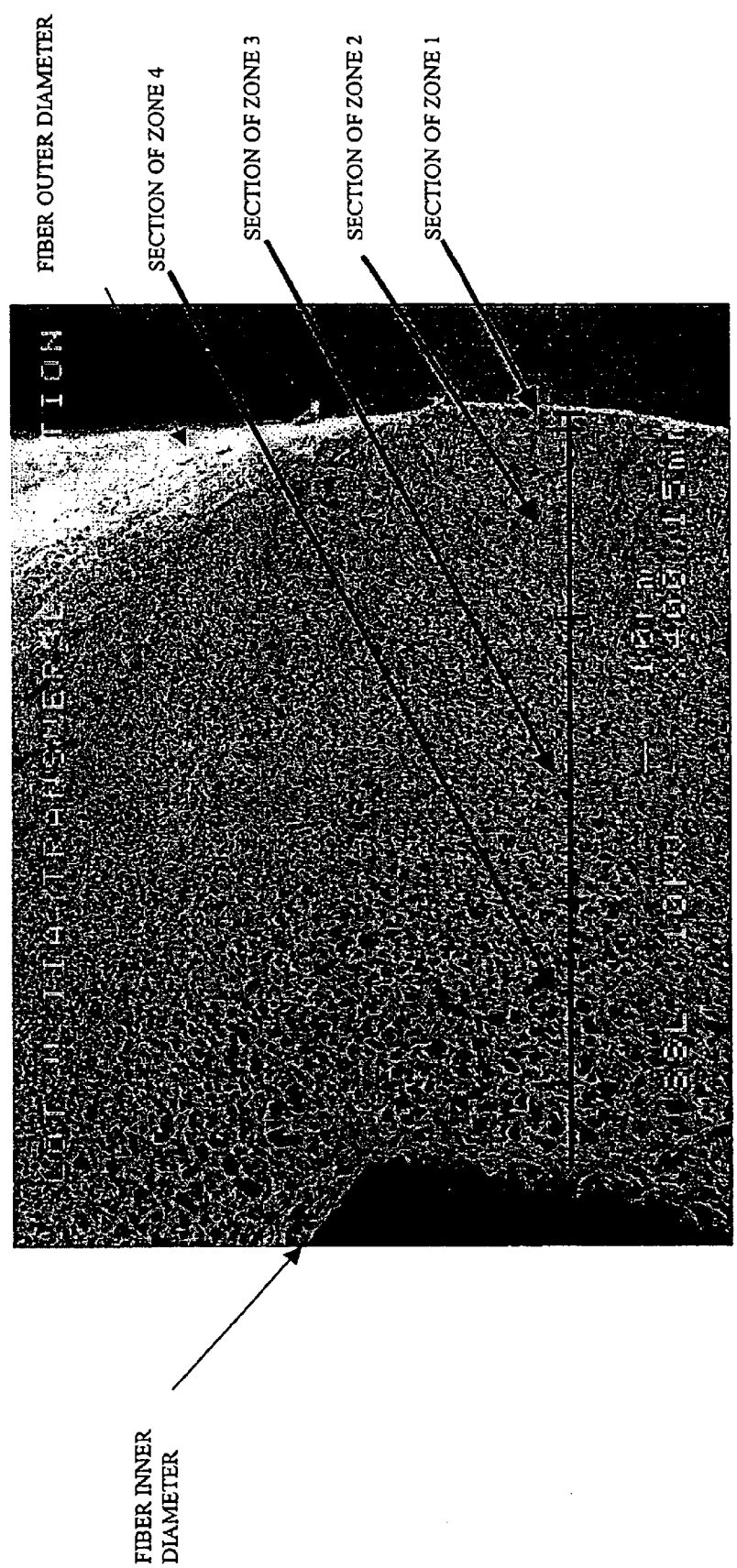
FIG. 8 is a SEM cross-section of a fiber of FIG. 7 at a magnification of 400 µm.

The fiber wall structure of the elongated microporous fibers is asymmetrical between the inner wall surface extending along the interior fiber lumen and the outer fiber wall surface exposed to blood in the vessel in which the filter device is implanted. The fiber wall at or adjacent to the outer wall surface has a higher mass density than the mass density adjacent to or at the inner wall surface. The mass density is a function of the average nominal pore size. Such asymmetric fiber wall morphology is illustrated in FIGS. 7 and 8, FIG. 7 showing a scanning electron microscopy (SEM) image of a cross-section of the fiber at 100 $\mu$m magnification. FIG. 8 shows a portion of the FIG. 7 fiber wall cross-section at a magnification of 400 $\mu$m. It will be observed that the structure of the fiber from the outer surface to the lumen is a continuous change in mass density whereby the pore size gradually changes between these fiber wall surfaces. However, it is convenient to describe the different mass density as sections or zones of the wall area having an average nominal pore size or average pore diameter, each zone having a different average nominal pore size. The walls may be characterized by two or more zones, for example 2, 3, or 4 or more mass density zones. The hollow fibers shown in FIGS. 7 and 8 are also shown and described in the aforesaid U.S. Pat. No. 6,802,820. In the fibers, the outer surface of the membrane, zone 1, has the highest mass density characterized by smaller average pore diameters. The outer zone forms the fiber interface with the permeate blood flow by determining filtration characteristics including the composition and components of separated plasma and controlling fiber membrane performance. Thus, zone 1 is the principle filtration portion of the fiber wall for controlling the trans-membrane flux (TMF) for excluding even the smallest cells in the blood, the platelets, having a diameter of about 1 $\mu$m. Nominal average pore diameters in zone 1 are between about 0.3 $\mu$m and about 1 $\mu$m, and preferably range from about 0.4 $\mu$m to about 0.8 $\mu$m. A preferred filtration sizing has a cutoff of about 0.6 $\mu$m to about 0.8 $\mu$m. Zones 2 and 2 are designed to decrease the flow path tortuosity and maintain the structural integrity required of the fiber exposed to physical conditions within the body. Pore size distribution in these zones ranges gradually from about 0.8 $\mu$m to about 1.2 $\mu$m and from about 1.2 $\mu$m to about 2.0 $\mu$m. Zone 2, having some flux-controlling pores, is principally to provide structural strength to the fiber as well as acting as a conduit for exudate flow to zone 3, also providing structure and enlarged pores for reducing the hydraulic resistance and providing a fluid conduit to the fiber lumen. The interior zones have little filtration function. Zone 4, representing the largest area having relatively large voids and pore diameters with little solid structure, has the primary function of a major reduction of hydraulic resistance through the membrane and defines the fiber inner lumen surface. Nominal average pore diameters in this lowest mass density zone are between about 1 $\mu$m and about 60 $\mu$m, and preferably between about 2 $\mu$m and about 6 $\mu$m. A typical fiber as shown has an OD of about 650 $\mu$m, an ID of about 250 $\mu$m and a wall thickness of about 250 $\mu$m. However, such dimensions are by way of example only. The fiber wall morphology, voids and pores may be further observed in U.S. Pat. No. 6,802,820, with figures illustrating the structures at magnifications of 1,000 $\mu$m and 5,000 $\mu$m.

The elongated microporous fibers used in the filter device may be produced using biocompatible polymers including those produced from polyurethane, polypropylene, polysulfone (polyethersulfone), polycarbonate, nylon, polyimide, as well as other synthetic resins known to those skilled in the art. A preferred polymer is polysulfone, and more preferably a polyethersulfone/polyethylene oxide copolymer with a polyethylene glycol solvent or a polysulfone modified with polyethylene oxide-polyethylene glycol copolymer. Such polysulfone fibers are produced in the presence of polymer dopes, core fluids, and coagulation fluids using processes including membrane spinning methods which achieve the desired product. Examples of such additive materials used in the polymerization process, spinning process and/or fiber membrane production include polyvinyl pyrrolidone, N-methyl pyrrolidone, dimethyl acetomide, dimethyl sulfoxide, and mixtures of two or more such materials. Such polysulfone fibers have been found to have the least detrimental characteristics that influence protein membrane interaction such as crystallinity, ionic groups, hydrogen bonding groups and hydrophobic sites. Specific methods for producing the aforesaid polymers and fibers are known to those skilled in the art and disclosed, for example, in PCT Publication WO 90/04609.

The filter device is used for carrying out in-vivo plasmapheresis in combination with a multiple lumen catheter, preferably a triple lumen catheter as illustrated in FIG. 6. The catheter is of a suitable length to provide for implanting or installing the filter device into the appropriate vessel of the patient, e.g., the inferior vena cava, between the diaphragm and the iliac junction via the femoral vein, jugular vein or subclavian vein. The catheter 20 may be secured to the proximal end 17 of the filter device 10 by a suitable method, e.g., using a suitable adhesive and an injection-molded connector 19. The catheter 20 has an access lumen 26 which is in open fluid communication with the interior of elongated hollow tubes 14 and 16 of the filter device. Return lumen 22 is occluded or blocked off at the distal end of the catheter 20, and is provided with one or more ports through the catheter wall near the distal end of the catheter whereby treated plasma may be returned to the patient. Backflush lumen 24 is also in open fluid communication with the interior of the hollow tubes 14 and 16 through which periodic backflush fluid is directed for preventing occlusion of the hollow fiber membrane caused by blood components. Such backflush procedure and apparatus are discussed in detail in U.S. Pat. No. 6,659,973, the description of which is incorporated herein by reference. The proximal end of the triple lumen catheter is secured to tubing components of a plasma separation system, such as disclosed in the aforesaid U.S. Pat. No. 6,659,973. The system includes plasma treatment apparatus for removing and/or separating selected plasma components and a fluid control assembly for directing plasma from the catheter to the treatment apparatus and return to the patient. The fluid control assembly also includes a pump for pumping plasma from the catheter to the treatment apparatus, a source of backflush fluid and a pump for pumping backflush fluid to the backflush lumen of the catheter. The fluid control apparatus also includes a microprocessor/controller for operating the pumps and controlling plasma flow rates and backflush fluid pressures, and backflush pumping intervals. The plasma treatment apparatus may be a single or multiple stage dialysate filter assembly or cascade membrane filters, absorbent cartridges, specialized adsorbent columns, chemical process or extraction assembly, or combinations, known to those skilled in the art.

Examples of medical applications for which the filter device described herein may be used include the following: therapeutic apheresis applications including plasma exchange, cascade protein separation by filtration, cascade protein removal or modification by adsorption cartridge, cryogenic modification, or chemical adaptation; fluid management application for congestive heart failure both acute and chronic; tissue engineering applications including online generation of media for bioreactor from xenogenic, allogenic, and autogenic sources; continuous renal replacement therapy (CRRT) for both acute and chronic kidney failure; edema prevention therapies for MODS (multiple organ dysfunction syndrome); cytokine removal or modification in therapy for septic shock or SIRS (systemic inflammatory response syndrome); plasma extraction from peritoneal ascites; intermittent hemodialysis (IHD) or hemodiafiltration; and ARDS (acute respiratory distress syndrome) therapy by reduction of pulmonary edema and physiological pulmonary dead space. Additional uses for the filter device of the present invention will be evident to those skilled in the art.

What is claimed is:

1. A filter device for being implanted in a blood vessel for carrying out in-vivo plasma separation comprising:
one or more elongated hollow tubes and a plurality of elongated microporous fibers having an interior lumen extending along the length thereof, each fiber having a first and second end secured to one or more of said elongated hollow tubes, wherein the interior lumen of each of the fibers communicates with the interior of one or more of the hollow tubes, and wherein each of the elongated microporous fibers have an asymmetrical fiber wall morphology between the inner wall surface extending along the interior fiber lumen and the outer wall surface, said fiber wall having a higher mass density zone adjacent to the outer wall surface and a lower mass density zone adjacent to the inner wall surface, said higher mass density zone having a smaller average nominal pore size than the average nominal pore size in the lower mass density zone and wherein said fibers are capable of separating plasma from whole blood by passing plasma through said fiber wall from the outer wall surface to the inner wall surface and to said interior lumen thereof.

2. A filter device of claim 1 comprising one or more first elongated hollow tubes and one or more second elongated hollow tubes extending substantially parallel along the length thereof, and wherein a first end of each of said elongated microporous fibers is secured to a first hollow tube and a second end of each of said fibers is secured to a second hollow tube whereby the interior fiber lumen of each fiber communicates with the interior of a first and a second hollow tube.

3. A filter device of claim 2 comprising two of said elongated hollow tubes, each of said tubes having a plurality of holes spaced apart along a substantial portion of the length thereof, each hole receiving a first or a second end of an elongated microporous fiber.

4. A filter device of claim 2 wherein the first and second ends of said elongated microporous fibers are secured to said first and second elongated hollow tubes in generally straight rows along the side of each of said tubes.

5. A filter device of claim 4 wherein the first hollow tube extends along a first axis and the second hollow tube extends along a second axis substantially parallel with said first axis, and wherein the first ends of said elongated microporous fibers are secured to said first hollow tube along a generally straight first row, and the second ends of said elongated microporous fibers are secured to said second hollow tube along a generally straight second row substantially parallel with said first row.

6. A filter device of claim 5 wherein the distance between said first and second rows is greater than the distance between said first and second axes.

7. A filter device of claim 6 wherein each of said fibers is generally bowed along its length between said first and second ends to form an arch spaced apart from said elongated hollow tubes and forming a passageway therebetween.

8. A filter device of claim 7 wherein the length of each of said hollow tubes along which fibers extend is between about 18 cm and about 22 cm and having about 6 fibers/cm of length of said hollow tubes, and wherein the space between adjacent fibers is between about 0.1 cm and about 1 cm.

9. A filter device of claim 7 wherein said elongated microporous fibers comprise first and second fibers, said first fibers forming a first arch of spaced fibers extending over a first portion of said device, said second fibers forming a second arch extending over a second portion of said device, opposite the first portion, said first and second arches spaced apart from said elongated hollow tubes to form passageways therebetween.

10. A filter device of claim 9 wherein first ends of first elongated microporous fibers are secured along a first row on a first hollow tube and second ends of first fibers are secured along a first row on a second hollow tube, and first ends of second fibers are secured along a second row on the first hollow tube and second ends of second fibers are secured along a second row on the second hollow tube, whereby said first and second fibers form opposite first and second arches, respectively, of spaced fibers along said device.

11. A filter device of claim 5, 6, 7, 9 or 10 wherein the first and second ends of said elongated microporous fibers are secured to said first and second hollow tubes, respectively, at substantially regular intervals.

12. A filter device of claim 11 wherein said regular intervals are between about 0.1 cm and about 1.0 cm.

13. A filter device of claim 11 wherein said regular intervals are between about 0.1 cm and about 0.3 cm.

14. A filter device of claim 12 wherein the length of each of said elongated microporous fibers is between about 1 cm and about 4 cm.

15. A filter device of claim 5, 6, 7, 9 or 10 wherein the length of each of said elongated microporous fibers is between about 1 cm and about 4 cm.

16. A filter device of claim 5, 6, 7, 9, or 10 wherein the first end of each elongated microporous fiber is offset longitudinally from the second end of each said fiber along the length of said elongated hollow tubes whereby a straight line extending through the first and second end of a fiber forms an acute angle with one of said axes.

17. A filter device of claim 16 wherein the space between adjacent fibers is between about 0.1 cm and about 1.0 cm.

18. A filter device of claim 16 wherein the space between adjacent fibers is between about 0.1 cm and about 0.3 cm.

19. A filter device of claim 16 wherein said acute angle is between about 45° and about 85°.

20. A filter device of claim 16 wherein said first and second ends of said elongated microporous fibers are secured to said first and second hollow tubes, respectively, at substantially regular intervals.

21. A filter device of claim 20 wherein adjacent first ends and adjacent second ends of said fibers are separated at regular intervals of between about 0.1 cm and about 0.3 cm.

22. A filter device of claim 16 wherein the length of each hollow tube is between about 10 cm and about 25 cm.

23. A filter device of claim 16 wherein the outer diameter of each hollow tube is between about 1 mm and about 3 mm.

24. A filter device of claim 16 wherein the length of each elongated hollow fiber is between about 1 mm and about 4 mm.

25. A filter device of claim 16 wherein the length of each hollow tube is between about 10 cm and about 25 cm, wherein the length of each elongated microporous fiber is between about 1 mm and about 4 mm, wherein the space between adjacent fibers is between about 0.1 cm and about 0.3 cm, and wherein said acute angle is between about 45° and about 85°.

26. A filter device of claim 16 having between 4 and 8 fibers/cm of the length of said hollow tubes.

27. A filter device of claim 16 having between 5 and 7 fibers/cm of the length of said hollow tubes.

28. A filter device of claim 27 wherein the length of each of said hollow tubes along which said fibers are secured is between about 15 cm and about 25 cm.

29. A filter device of claim 27 wherein the length of each of said hollow tubes along which said fibers are secured is between about 18 cm and about 22 cm.

30. A filter device of claim 1 wherein said fiber wall has two mass density zones and wherein each of said zones is characterized by a different average nominal pore size.

31. A filter device of claim 30 wherein the nominal average pore diameter in said lower mass density zone is between about 2 $\mu$m and about 6 $\mu$m.

32. A filter device of claim 31 wherein the nominal average pore diameter in said higher mass density zone is between about 0.4 $\mu$m and about 0.8 $\mu$m.

33. A filter device of claim 32 having one or more intermediate mass density zones having a nominal average pore diameter of between about 0.8 $\mu$m and about 2 $\mu$m.

34. A filter device of claim 33 having two intermediate mass density zones, a first intermediate zone having a nominal average pore diameter of between about 0.8 $\mu$m and about 1.2 $\mu$m and a second intermediate zone having a nominal average pore diameter of between about 1.2 $\mu$m and about 2 $\mu$m.

35. A filter device of claim 33 wherein said fibers comprise a polysulfone fiber.

36. A filter device of claim 1, wherein the fiber wall structure comprises a continuous change in mass density between the inner and outer wall surfaces of the fiber.

37. A filter device of claim 1, or 33 wherein distal and proximal elongated fibers are substantially filled with a synthetic resin.

38. A filter device of claim 33, wherein the fiber wall structure comprises a continuous change in mass density between the inner and outer wall surface of the fiber.

39. A filter device of claim 30 wherein the nominal average pore diameter in said higher mass density zone is between about 0.4 $\mu$m and about 0.8 $\mu$m.

40. A filter device of claim 1 wherein said fiber wall has three mass density zones and wherein each of said zones is characterized by a different average nominal pore size.

41. A filter device of claim 1 wherein said fiber wall has four or more mass density zones and wherein each of said zones is characterized by a different average nominal pore size.

42. A filter device of claim 30, 40 or 41 wherein said lower mass density zone is characterized by a nominal average pore diameter of between about 1 μm and about 60 μm.

43. A filter device of claim 42 wherein said higher mass density zone is characterized by a nominal average pore diameter of between about 0.3 μm and about 1 μm.

44. A filter device of claim 43, wherein the fiber wall structure comprises a continuous change in mass density between the inner and outer wall surface of the fiber.

45. A filter device of claim 42 capable of in-vivo ultra-filtration wherein said higher mass density zone is characterized by a nominal average pore diameter of between about 0.005 μm and about 0.05 μm.

46. A filter device of claim 42, wherein the fiber wall structure comprises a continuous change in mass density between the inner and outer wall surface of the fiber.

47. A filter device of claim 30, 40 or 41 wherein said higher mass density zone is characterized by a nominal average pore diameter of between about 0.3 μm and about 1 μm.

48. A filter device of claim 47, wherein the fiber wall structure comprises a continuous change in mass density between the inner and outer wall surface of the fiber.

* * * * *

UNITED STATES PATENT AND TRADEMARK OFFICE
CERTIFICATE OF CORRECTION

PATENT NO. : 6,899,692 B2
DATED : May 31, 2005
INVENTOR(S) : Gorsuch et al.

It is certified that error appears in the above-identified patent and that said Letters Patent is hereby corrected as shown below:

Column 4,
Line 58, after "and" delete "2" and insert -- 3 --.

Column 7,
Line 62, after "9" delete ",".

Column 8,
Lines 56 and 59, after "claim 1" delete ",".

Signed and Sealed this

Fourteenth Day of March, 2006

JON W. DUDAS
*Director of the United States Patent and Trademark Office*